(12) United States Patent
Marler

(10) Patent No.: US 8,591,480 B2
(45) Date of Patent: Nov. 26, 2013

(54) SURGICAL CANNULA

(76) Inventor: Gregory S. Marler, Rockford, IL (US)

( * ) Notice: Subject to any disclaimer, the term of this patent is extended or adjusted under 35 U.S.C. 154(b) by 314 days.

(21) Appl. No.: 12/814,971

(22) Filed: Jun. 14, 2010

(65) Prior Publication Data

US 2011/0306951 A1    Dec. 15, 2011

(51) Int. Cl.
*A61M 5/00*      (2006.01)

(52) U.S. Cl.
USPC ......................................................... 604/264

(58) Field of Classification Search
USPC ......................................................... 604/264
See application file for complete search history.

(56) References Cited

U.S. PATENT DOCUMENTS

| | | | |
|---|---|---|---|
| 4,784,649 A | | 11/1988 | Imonti et al. |
| 4,925,450 A | * | 5/1990 | Imonti et al. ................... 604/240 |
| 4,985,027 A | * | 1/1991 | Dressel ............................ 606/15 |
| 5,052,999 A | * | 10/1991 | Klein ............................... 604/19 |
| 5,102,410 A | * | 4/1992 | Dressel ............................ 606/15 |
| 5,181,907 A | * | 1/1993 | Becker ............................ 604/22 |
| 5,242,386 A | * | 9/1993 | Holzer ............................ 604/22 |
| 5,744,360 A | * | 4/1998 | Hu et al. ........................ 435/366 |
| 5,766,194 A | * | 6/1998 | Smith ............................ 606/167 |
| 5,817,050 A | | 10/1998 | Klein |
| 5,911,700 A | * | 6/1999 | Mozsary et al. ................ 604/22 |
| 6,007,540 A | * | 12/1999 | Ark ................................. 606/80 |
| 6,020,196 A | * | 2/2000 | Hu et al. ........................ 435/366 |
| 6,090,121 A | * | 7/2000 | Weber et al. ................... 606/170 |
| 6,102,885 A | * | 8/2000 | Bass ............................... 604/22 |
| 6,106,516 A | * | 8/2000 | Massengill ..................... 606/15 |
| 6,120,519 A | * | 9/2000 | Weber et al. ................... 606/170 |
| 6,344,038 B1 | | 2/2002 | Weber |
| 6,394,973 B1 | * | 5/2002 | Cucin ............................. 604/22 |
| 6,464,694 B1 | * | 10/2002 | Massengill ..................... 606/15 |

(Continued)

FOREIGN PATENT DOCUMENTS

| | | |
|---|---|---|
| KR | 10-2009-0068497 A | 6/2009 |
| KR | 20-2009-0008627 U | 8/2009 |

OTHER PUBLICATIONS

Byron Medical Inc., Online Catalog, Cannulae & Dissectors, 2004, Wayback Machine, http://web.archive.bibalex.org/web/*/http://byronmedical.com, Apr. 20, 2006.*

(Continued)

*Primary Examiner* — Leslie Deak
*Assistant Examiner* — Guy K Townsend
(74) *Attorney, Agent, or Firm* — Reinhart Boerner Van Deuren P.C.

(57) ABSTRACT

A surgical cannula and method may be constructed in disposable or reusable forms, and may have at least one outwardly extending projection or rib along an outer surface of a tubular shaft. Such a rib, or ribs, may also extend along an outer surface of a cannula tip. A bore in the tubular shaft may have a substantially circular cross-sectional shape, or alternatively in embodiments with outwardly extending ribs may be non-circular and include at least one lobe extending outward into at least one outwardly projecting rib. Some embodiments also include apertures having peripheries that are at least partly configured to form cutting edges.

40 Claims, 13 Drawing Sheets

(56) References Cited

U.S. PATENT DOCUMENTS

| | | | |
|---|---|---|---|
| 6,530,125 B2* | 3/2003 | Shippert | 16/430 |
| 6,544,248 B1* | 4/2003 | Bass | 604/511 |
| 6,562,054 B1* | 5/2003 | Weber et al. | 606/170 |
| 6,638,238 B1* | 10/2003 | Weber et al. | 604/22 |
| 6,676,677 B2* | 1/2004 | Klein | 606/171 |
| 6,817,996 B2 | 11/2004 | Fard et al. | |
| 6,872,199 B2* | 3/2005 | Cucin | 604/542 |
| 6,875,207 B2* | 4/2005 | Weber et al. | 604/542 |
| 6,902,559 B2* | 6/2005 | Taufig | 604/542 |
| 6,918,903 B2 | 7/2005 | Bass | |
| 7,018,354 B2 | 3/2006 | Tazi | |
| 7,056,315 B2 | 6/2006 | Gonon et al. | |
| 7,462,176 B2* | 12/2008 | Bass | 604/511 |
| 8,043,253 B2* | 10/2011 | Kraft et al. | 604/35 |
| 2002/0169469 A1 | 11/2002 | Klein | |
| 2003/0009854 A1* | 1/2003 | Shippert | 16/430 |
| 2003/0125681 A1* | 7/2003 | Fard et al. | 604/353 |
| 2003/0167053 A1* | 9/2003 | Taufig | 604/542 |
| 2003/0176851 A1* | 9/2003 | Bass | 604/542 |
| 2003/0187383 A1* | 10/2003 | Weber et al. | 604/22 |
| 2004/0044331 A1* | 3/2004 | Klein | 604/542 |
| 2005/0256498 A1* | 11/2005 | Bass | 604/500 |
| 2006/0235456 A1* | 10/2006 | Luz | 606/190 |
| 2006/0241567 A1* | 10/2006 | Schaffer | 604/542 |
| 2007/0093755 A1* | 4/2007 | Koos et al. | 604/164.01 |
| 2007/0156161 A1* | 7/2007 | Weadock et al. | 606/170 |
| 2008/0167613 A1* | 7/2008 | Khouri et al. | 604/119 |
| 2008/0188833 A1* | 8/2008 | Taufig | 604/540 |
| 2009/0143717 A1* | 6/2009 | Bass | 604/22 |

OTHER PUBLICATIONS

Mentor, Byron Medical Inc.; "Infiltration Handles", pamphlet, p. 25, known prior to Jun. 14, 2010.

Mentor, Byron Medical Inc.; "LAMIS Infiltration Cannulae," pamphlet, p. 26, known prior to Jun. 14, 2010.

Mentor, Byron Medical Inc.; "Cannula Products," pamphlet, p. 30, known prior to Jun. 14, 2010.

Mentor, Byron Medical Inc., "Cannula Tip Styles," pamphlet, p. 31, known prior to Jun. 14, 2010.

Mentor, Byron Medical Inc., "Cannula Products," pamphlet, p. 32, known prior to Jun. 14, 2010.

Mentor, Byron Medical Inc., "ARC-HII Reciprocating Cannula," pamphlet, p. 33, known prior to Jun. 14, 2010.

Mentor, Byron Medical Inc., "Luer Lock Cannula Series," pamphlet, p. 36, known prior to Jun. 14, 2010.

Mentor, Byron Medical Inc., "Luer Lock Micro-Cannula Series," pamphlet, p. 37, known prior to Jun. 14, 2010.

Mentor, Byron Medical Inc., "The Concorde Series," pamphlet, p. 38, known prior to Jun. 14, 2010.

Mentor, Byron Medical Inc., "Disposable Cannula Brushes," pamphlet, p. 40, known prior to Jun. 14, 2010.

Mentor, Byron Medical Inc., "Coleman Microinjection System," pamphlet, p. 46, known prior to Jun. 14, 2010.

Mentor, Byron Medical Inc., "Coleman Microinjection System," pamphlet, p. 47, known prior to Jun. 14, 2010.

* cited by examiner

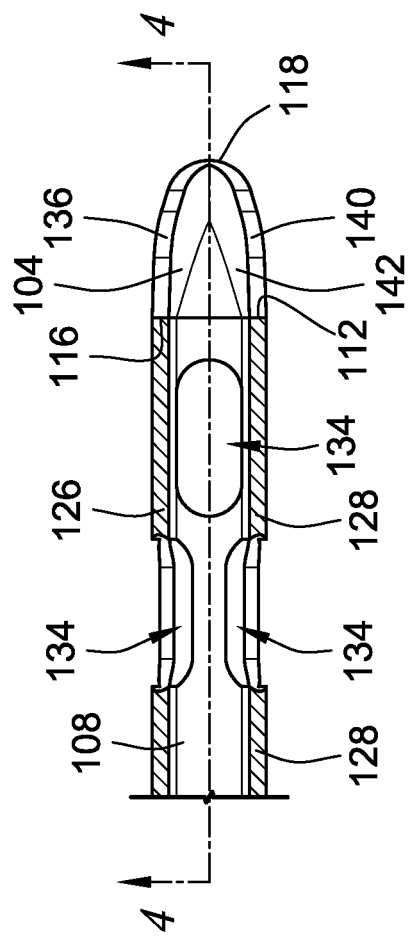
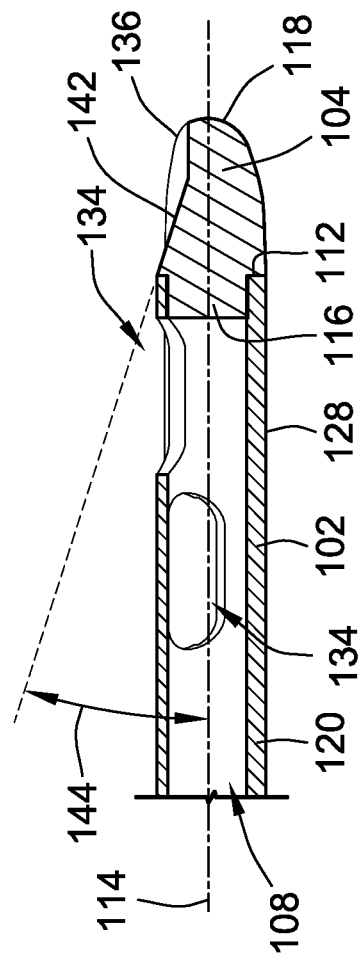

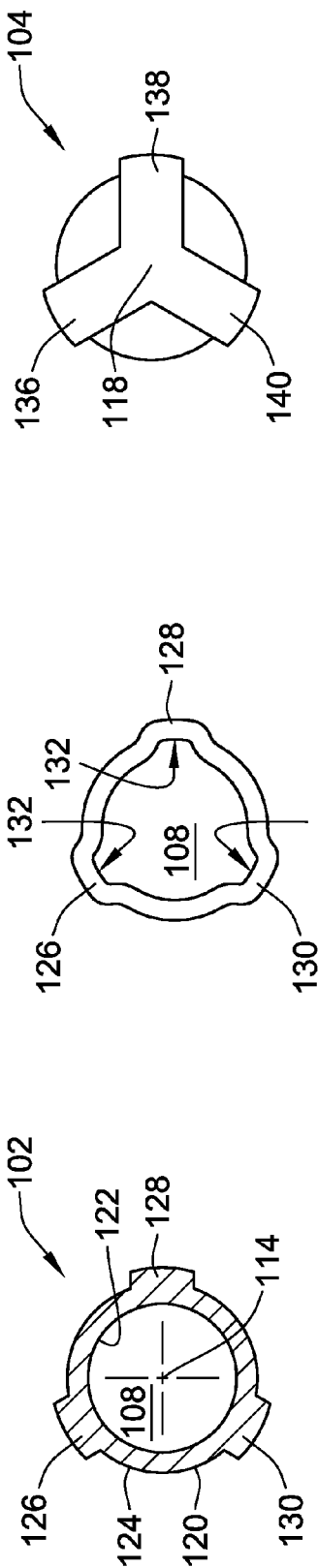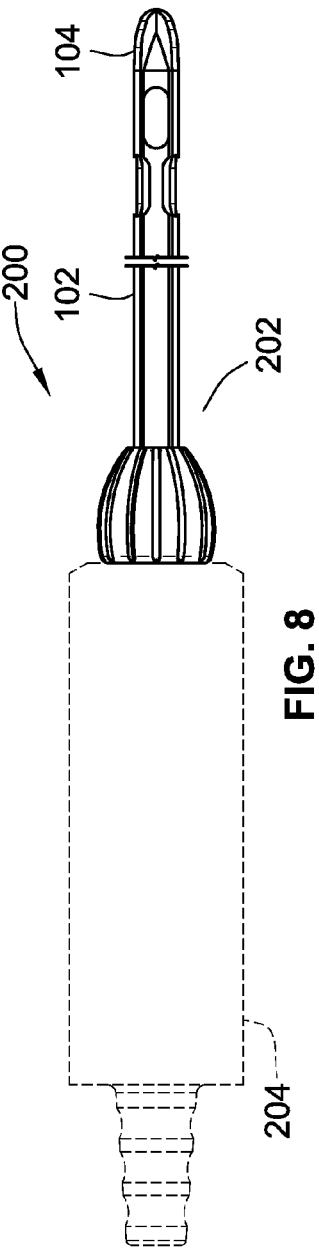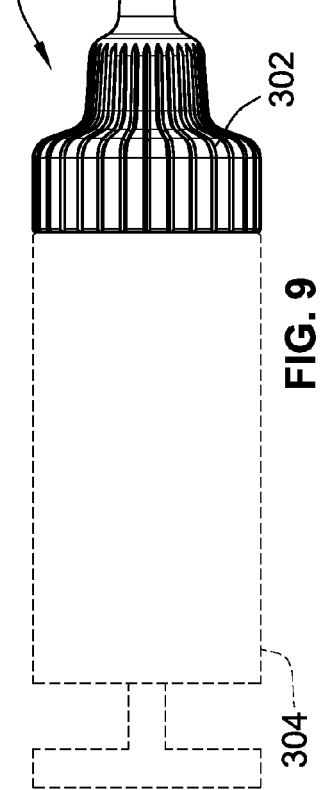

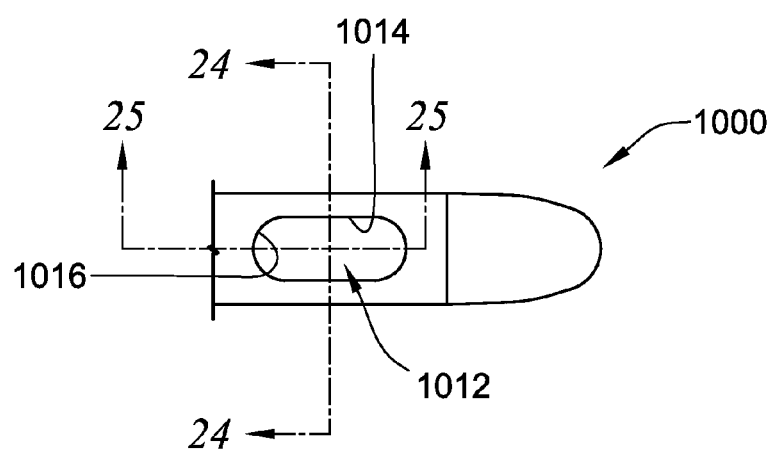
FIG. 23
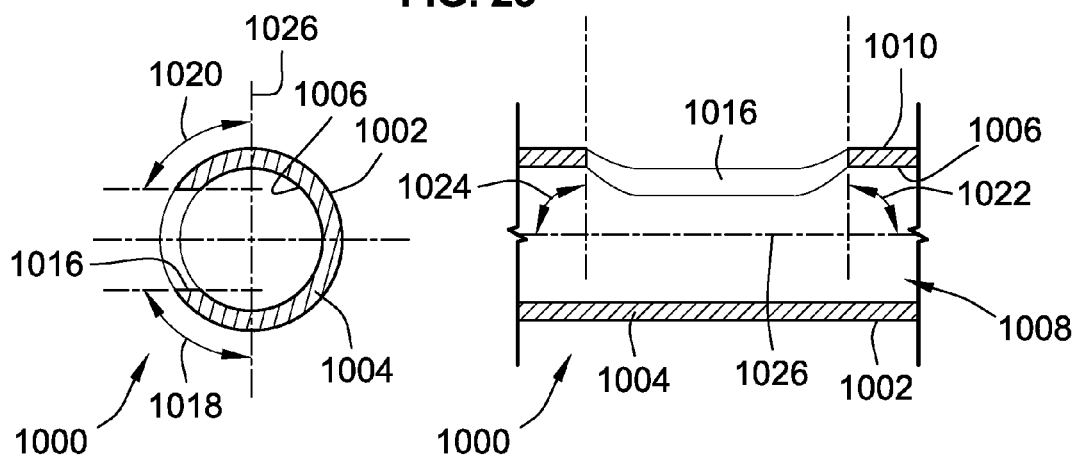
FIG. 24     FIG. 25

SURGICAL CANNULA

FIELD OF THE INVENTION

This invention relates generally to a surgical cannula and the use thereof, and more particularly to a surgical cannula for use in breaking up, infiltrating and aspirating tissues during surgical procedures such as liposuction.

BACKGROUND OF THE INVENTION

Surgical cannulas have been used for many years to perform a variety of surgical procedures, such as liposuction.

To perform liposuction, for example, a hand-held instrument (known as a cannula) is inserted through a portal or incision in the patient's skin and into pockets of fat located between the patient's skin and muscles. Once inserted below the skin and into the fat pockets, the cannula is moved around by the surgeon to break up the fat cells. Parcels of the fat tissue are then aspirated through small openings along the sides of the cannula by vacuum applied by a syringe or a pump. The fat tissue is drawn through a central bore, known as a lumen, in the cannula, to a tissue canister connected in fluid communication between the cannula and the suction source.

A typical cannula, of the type used for liposuction, for example, includes an elongated tubular shaft, closed by a cannula tip at the distal end of the shaft which is inserted through the patient's skin. The aspirator tip, and shaft, may include small openings along the sides or at the end of the tip, to create a passage for movement of the tissue to be removed into the central bore of the cannula. The end of the tubular shaft opposite from the cannula tip is typically equipped with a surgical handle to be grasped by the surgeon or a fitting for connecting the cannula to a syringe or other vacuum source. The end of the cannula having the handle or fitting may also be configured for attachment to an infiltration syringe or other source of infiltration fluid.

During use, the vacuum created by suction within the bore of the cannula causes tissue to be pulled into the openings along the sides and at the aspirator tip of the cannula. In some procedures, a cannula of the type described hereinabove may also be used for injecting a fluid into the tissue, in a procedure known as infiltration or tumescent infiltration.

In use, therefore, a typical surgical cannula performs one or more of three basic functions. First, the cannula is used to penetrate, crush, tear, or avulse the fatty tissue in such a manner that it can be suctioned through the openings into the central bore of the cannula. Secondly, the cannula may be used to suction fatty tissue through the central bore to aspirate tissue fragments and fluids from the operative site. Thirdly, the cannula may be used for infiltrating the operative site with a fluid to facilitate breaking up and removing the fatty tissue. It is desirable to provide an improved cannula and method of use for a cannula which enhances the performance of any of these basic functions of the cannula. It is also desirable to provide an improved cannula which is safer for the patient, and which reduces fatigue on the surgeon performing a procedure utilizing the cannula.

It is specifically desirable to provide an improved cannula and method for use having an improved ability to effectively remove, crush, tear or avulse fatty tissue at the operative site. It has been noted that, during aspiration of fatty tissue and fluids from the surgical site, a seal can be created between the outer surface of prior cannulas and the fatty tissue which inhibits the flow of any ambient pressure fluid, such as air, to the operative site about the tip of the cannula. When suction is applied, such a seal prevents the flow of any ambient pressure fluid to the operative site about the shaft or tip of the cannula. When this occurs, the suction capacity of the cannula is substantially reduced, and the fatty tissue fragments and fluids move more slowly than is desirable through the cannula and any related suction equipment to the tissue canister.

Another area in which improvement is desirable, is the cost of such surgical cannulas. Primarily as a cost-saving measure, prior surgical cannulas are typically reused for multiple patients, with the cannulas being subjected to sterilization by steam, or other methods between uses. Although such sterilization has generally been sufficient to protect the subsequent patients, it is well-known that, due to the construction of a typical cannula, small tissue fragments may remain inside the cannula. It has also been prior practice in reusing cannulas to subject the cannulas to enzymatic cleaning agents, germicides, disinfectants, and other cleaning agents, which may also be partly retained inside the cannula. These residual tissue particles and/or chemical agents potentially subject the subsequent patient to an increased risk of complications during, or following a surgical procedure. It is highly desirable, therefore, to provide a surgical cannula and method which does not require or rely upon reuse of the cannulas.

It is also desirable that an improved cannula be configured and adapted for interchangeable use with commonly available suction and tissue removal, or aspiration equipment.

It is also desirable that an improved cannula be configured and adapted for interchangeable use with commonly available infiltration equipment.

BRIEF SUMMARY OF THE INVENTION

This invention provides an improved surgical cannula, and method for its use, offering significant advantages over prior cannulas and methods. These improvements include, but are not limited to, enhanced performance of the cannula during surgical procedures, greater safety for the patient and medical personnel, and a cannula that is also easier for the surgeon to use with lessened fatigue during the surgical procedure.

In one form of the invention, a surgical cannula includes an elongated tubular shaft having a wall extending about a longitudinal axis of the cannula. The wall has an inner surface thereof defining a bore extending longitudinally through the cannula from a proximal to a distal end of the tubular shaft. The tubular shaft may also have at least one outwardly projecting rib extending substantially longitudinally along an outer surface of the tubular shaft. In some forms of the invention, the bore in the tubular shaft may have a substantially circular cross-sectional shape. In other embodiments of the invention, the bore may have a substantially non-circular cross-sectional shape. In some forms of the invention, the bore may include at least one lobe thereof, with the at least one lobe extending outward into at least one outwardly projecting rib.

In some forms of the invention, the at least one outwardly projecting rib may be substantially straight and extend longitudinally along the entire length of the tubular shaft of the cannula, from a proximal to a distal end of the tubular shaft. In other embodiments of the invention, a rib may extend substantially the full length of the tubular shaft, but not be straight. Specifically, such a non-straight rib may follow a helical or other path. In yet other embodiments of the invention, the one or more ribs extending from the outer surface of the tubular shaft may be intermittent along the longitudinal length of the tubular shaft. In some forms of the invention, outwardly extending ribs may include a variety of these various forms and shapes.

A surgical cannula, according to the invention, may include one or more apertures extending through the wall of the tubular shaft. These apertures may be disposed in relation to one of the at least one projecting ribs. In some forms of the invention at least one of the apertures may have a peripheral edge thereof that is at least partly configured to form a cutting edge, to thereby enhance cutting action and reduce the force required to cut away portions of the tissue during manipulation of the cannula. In some forms of the invention only one or both longitudinal ends of an aperture may be configured to form a cutting edge so that the cutting edge is only primarily effective during a push and/or pull stroke of the cannula. In other forms of the invention only one or both longitudinally extending sides of an aperture may be configured to form a cutting edge so that the cutting edge is only primarily effective during a rotational motion of the cannula. In other forms of the invention, the edge of the aperture may be configured to include other combinations of cutting edges on all or only portions of the periphery to be primarily effective on a variety of motions of the cannula. Those having skill in the art will recognize that regardless of the position of the cutting edge along the periphery of the aperture, overall cutting action will be enhanced and the force required to manipulate the cannula during tissue cutting will be reduced.

In some forms of the invention, a cannula may include one or more portions thereof that include tactilely or visually discernable surface treatments or indicia thereupon to aid the surgeon in positioning the cannula in a desired orientation while portions of the tubular shaft of the cannula are not otherwise visible, due to being inserted under the skin of a patient. These indicia may be positioned on the handle, fitting and/or on the tubular shaft, in some forms of the invention, for example, to aid the surgeon in knowing the orientation of the apertures in the cannula.

In some forms of the surgical cannula, according to the invention, the tubular shaft may include a plurality of outwardly projecting substantially longitudinally extending ribs, with a rib or ribs from which the apertures are positioned being visually discernable from the other ribs. The visually discernable rib or ribs may have a unique shape, texture, or bear some form of indicia or colored marking to aid in visual discernment of this particular rib from the other ribs.

In some forms of the invention having a plurality of outwardly projecting substantially longitudinally extending ribs, a rib or ribs from which the apertures are positioned may be tactilely discernable from the other ribs, so that the surgeon may determine the orientation of this particular rib through touch, rather than visually. In some forms of the invention having longitudinally extending ribs and a handle or fitting at the proximal end of the tubular shaft, the handle or fitting may include tactilely and/or visually discernable indicia oriented in correspondence with the aperture and/or the rib from which the apertures are positioned to aid the surgeon in knowing the orientation of apertures in the cannula. In some forms of the invention having such a handle or fitting, the rib from which the apertures are positioned may, or may not, be tactilely and/or visually discernable from the other ribs.

In some forms of the invention, the bore at the distal end of the tubular shaft of the cannula may be closed by a cannula tip. In some forms of the invention, the cannula tip may include a rib tip extending from a proximal end of the cannula tip, with the proximal end of the cannula tip being attached to the distal end of the tubular shaft. Such a rib tip may extend from the proximal end of the cannula tip to a distal end of the cannula tip, in some forms of a rib tip according to the invention. Where the tubular shaft of a cannula, according to the invention, includes a plurality of longitudinally extending ribs, a cannula tip, according to the invention, may include a plurality of rib tips with each of the plurality of rib tips of the cannula tip corresponding to and extending one of the plurality of ribs of the tubular shaft along the cannula tip from a proximal end of the cannula tip to a distal end of the cannula tip. The plurality of rib tips extending along the cannula tip may converge with one another at the distal end of the cannula tip, in some forms of the invention. The rib tips may also define a blunted surface at the distal end of the cannula tip.

In some forms of a cannula tip having multiple rib tips, according to the invention, the cannula tip may further define a substantially conical outer surface thereof between the rib tips such a conical surface may define a conic angle in the range of 10 degrees to 30 degrees.

A cannula tip, according to the invention, may also define a substantially convex-curved outer surface between the plurality of the rib tips. A cannula tip having either a conical-shaped outer surface, or a convex-curved outer surface between the rib tips may include apertures extending through a wall of the tip in fluid communication with the bore in the tubular shaft.

In some forms of the invention, a cannula tip closing the bore at the distal end of the tubular shaft may be joined to the tubular shaft by a mechanical connection. Such mechanical connections may include an arrangement utilizing: a press-fit; a snap fit; a pinned connection; a retainer ring; a crimped or formed joint; or any other appropriate form of mechanical connection. In other forms of the invention, a cannula tip may be joined to the distal end of the tubular shaft by an adhesive. In yet other forms of the invention, a cannula tip may be joined to the distal end of the tubular shaft by processes such as welding or brazing.

At least one of the inner and outer surfaces of the tubular shaft of a cannula, according to the invention, may include a low-friction coating. In embodiments of the invention having a cannula tip closing the bore in the tubular shaft at a distal end of the tubular shaft, both the cannula tip and the cannula shaft may have at least a portion thereof including a low-friction coating.

A surgical cannula, according to the invention, may include at least one portion thereof which is not steam-sterilizable. As used herein, it is contemplated that the term "not steam-sterilizable" means that exposure to steam sterilization will deform the portion of the cannula not capable of withstanding steam sterilization to such a degree that the surgical cannula is no longer usable.

In some forms of the invention, the cannula may be at least partly formed form a non-metallic material. Where such a non-metallic material is utilized, a portion of the cannula which may be inserted into a patient may be formulated from a material which is also radio opaque. It is contemplated that the use of such a radio opaque non-metallic material would facilitate locating and removal of that portion of the cannula should it separate from the remainder of the cannula during use.

In forms of the invention which are not steam-sterilizable, it is contemplated that one or more portions of such a cannula, such as the tubular shaft, the cannula tip, any handle or connectors for attachment to a fluid source may be formed at least partly from a material which is not steam-sterilizable.

Some forms of a surgical cannula, in accordance with the invention may include a connector attached to the proximal end of the tubular shaft and having a fluid passage defined thereby connected in fluid communication with the bore in the tubular shaft. The connector may take any appropriate form, including a connector from the group consisting of: a hose barb; a Toomey hub; a Luer lock or other surgical connector. In some forms of the invention, the connector may be part of a handle attached to the proximal end of the tubular shaft.

Some forms of a surgical cannula, in accordance with the invention, may include portions thereof formed from bioplastic. For example, in some forms of the invention having a handle, the handle may be formed at least partly from a bioplastic.

The invention may also take the form of a method for performing a surgical procedure, by inserting a cannula having at least one outwardly longitudinally extending rib into the tissue and manipulating the cannula. Such a method may also include infiltrating the tissue at the operative site, in coordination with manipulation of the cannula. A method may alternatively or additionally include aspirating the tissue at the operative site in coordination with manipulation of the cannula.

Those having skill in the art will recognize that the invention may be practiced in a wide variety of forms, including one or more of the aspects of the invention described above. Those skilled in the art will appreciate that a cannula and method, according to the invention, provides a significant advantage over prior cannulas, in forms of the invention having one or more ribs on the outside of the tubular shaft, in that as the cannula is moved by the surgeon, the rib will facilitate crushing, tearing or otherwise avulsing the fatty tissue. The rib also lessens the propensity to form a seal between the cannula and the surrounding tissue, thereby facilitating aspiration of the tissue fragments and fluids from around the cannula.

In forms of the invention having a bore in the tubular shaft including lobes extending out into the ribs on the outside of the tubular shaft, it will be appreciated that the lobes substantially increase the internal cross-sectional flow area of the bore in a manner that facilitates rapid transfer of the removed tissue and fluids from the operative site to the tissue container.

The shape of the cannula tip and tubular shaft, according to the invention, have been selected to reduce the force that must be applied by a surgeon to manipulate the cannula during use. This reduction in force results in less arm and shoulder fatigue for the surgeon during the process.

Through practice of the invention, it is also contemplated that a cannula can be produced at a low enough cost to be essentially disposable, thereby eliminating the risk to the patient of a reaction to biological or chemical residues within a cannula that has previously been used. The various aspects of the invention resulting in a cannula which cannot be reused after steam-sterilization provides yet further protection for the patient and medical professional.

These and other aspects, objects and advantages of the invention will be apparent from the following detailed description and accompanying drawings describing exemplary embodiments of the invention.

BRIEF DESCRIPTION OF THE DRAWINGS

The accompanying drawings incorporated in and forming a part of the specification illustrate several aspects of the present invention and, together with the description, serve to explain the invention. In the drawings:

FIGS. 2-7 are cross-sectional and enlarged views illustrating details of the first exemplary embodiment of the surgical cannula shown in FIG. 1.

FIG. 8 illustrates a second exemplary embodiment of a surgical cannula having ribs extending along a tubular shaft and a cannula tip, according to the invention, but having the proximal end of the tubular shaft of the cannula terminating in a Luer fitting, or other surgical connector for attachment to an infiltration handle or syringe.

FIG. 9 illustrates a third exemplary embodiment of a surgical cannula having ribs extending along a tubular shaft and a cannula tip, according to the invention, but having the proximal end of the tubular shaft of the cannula terminating in a Toomey hub, for attachment to a Toomey syringe.

FIGS. 23-25 are enlarged views illustrating details of an aperture in a cannula, according to the invention, having the entirety of an aperture edge configured at substantially a right angle to a median plane of the cannula.

While the invention will be described in connection with certain preferred embodiments, there is no intent to limit it to those embodiments. On the contrary, the intent is to cover all alternatives, modifications and equivalents as included within the spirit and scope of the invention.

DETAILED DESCRIPTION OF THE INVENTION

Figure 1:
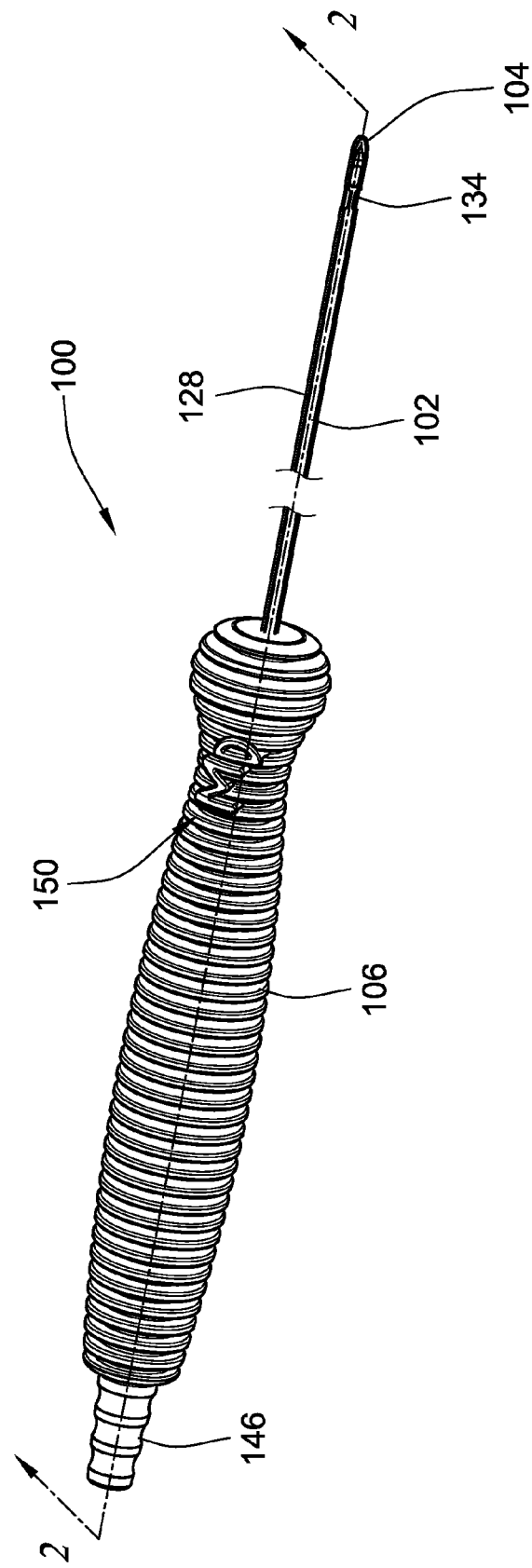
FIG. 1 is a perspective illustration of a first exemplary embodiment of a surgical cannula, according to the invention, having a plurality of ribs extending along a tubular shaft of the surgical cannula and terminating in a corresponding series of rib tips which converge at a distal end of the surgical cannula.
Figure 2:
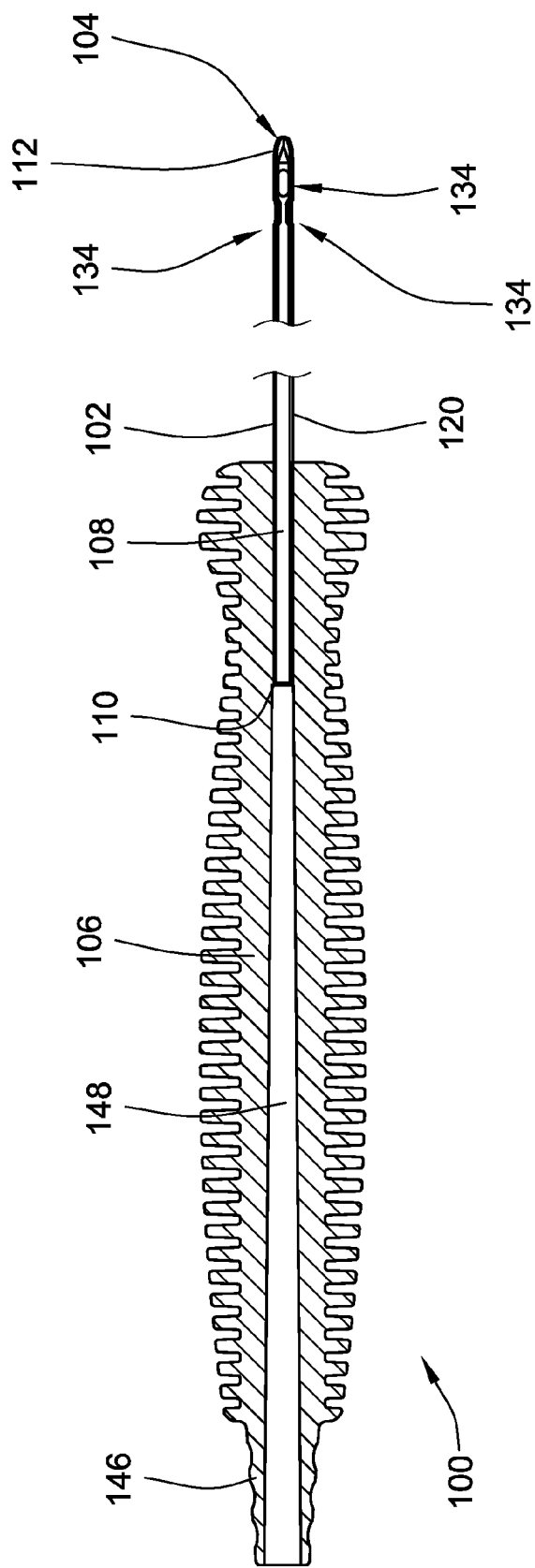
Figure 10:
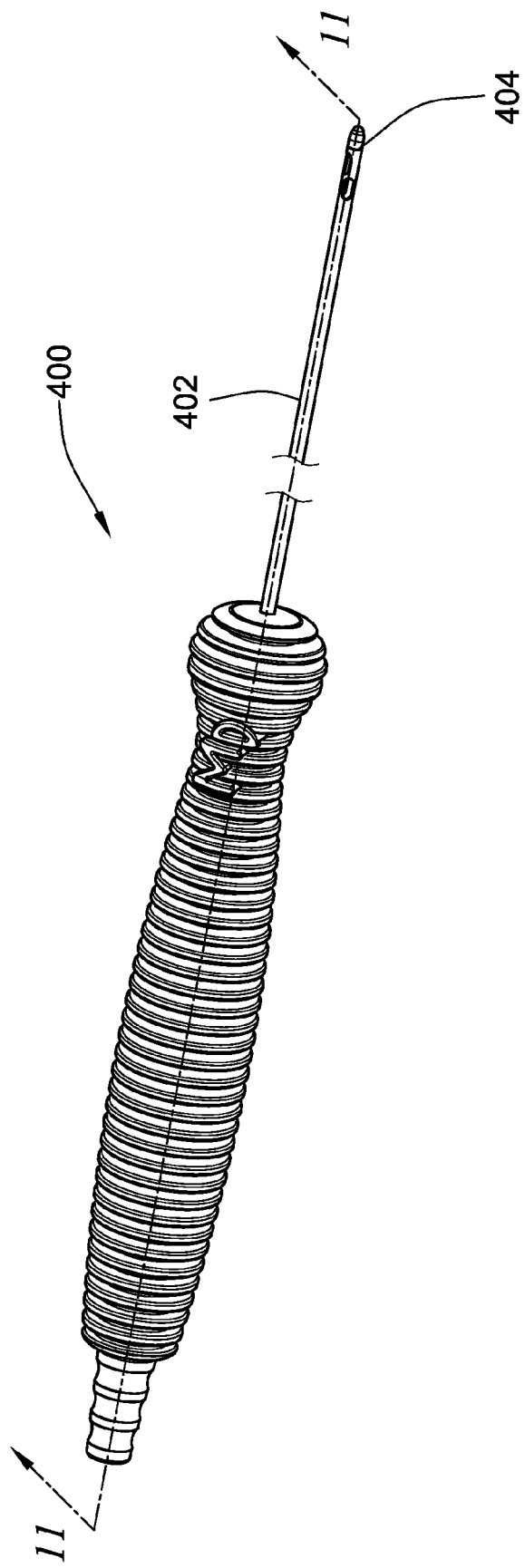
FIG. 10 is a fourth exemplary embodiment of the invention, substantially similar to the first exemplary embodiment of FIGS. 1-7, with the exception that the exemplary embodiment of FIG. 10 does not include ribs extending longitudinally along either the tubular shaft or the tip of the cannula.
Figure 11:
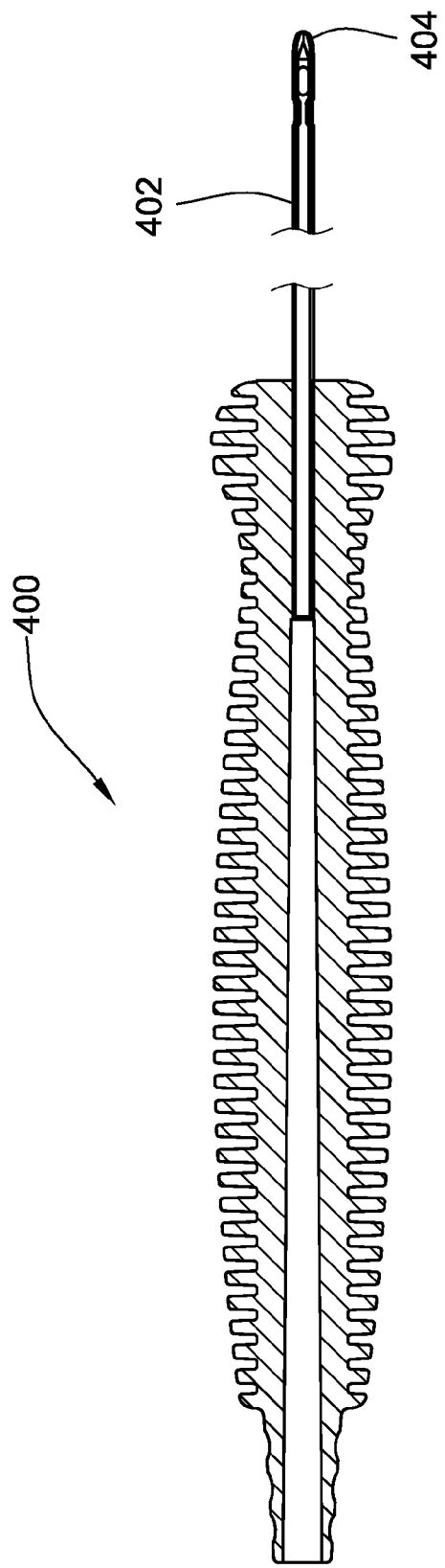
FIGS. 11-14 are cross-sectional and enlarged views of portions of the fourth exemplary embodiment of the cannula, according to the invention, shown in FIG. 10.

FIGS. 1 and 2 show a first exemplary embodiment of a surgical cannula 100, according to the invention, having a tubular shaft 102, a cannula tip 104, and a handle arrangement 106. The tubular shaft 102 defines a bore or lumen 108 in the tubular shaft 102 extending from a proximal end 110 to a distal end 112 of the tubular shaft 102 along a longitudinal axis 114 of the cannula 100.

As shown in FIGS. 3 and 4, the cannula tip 104 closes the bore 108 at the distal end 112 of the tubular shaft 102. As best seen in FIG. 4, in the first exemplary embodiment of a surgical cannula 100, according to the invention, the cannula tip 104 is attached to the tubular shaft 102 by a press-fit arrangement, in which a portion of the proximal end 116 of the cannula tip 104 is inserted into the bore 108 at the distal end 112 of the tubular shaft 102. Once the tip 104 is thus attached, a distal end 118 of the cannula tip 104 also forms a distal end of the surgical cannula 100.

Although the cannula tip 104 is attached to the tubular shaft 102 by a press-fit arrangement in the first exemplary embodiment of the surgical cannula 100, it is contemplated that in other embodiments of the invention a cannula tip may be attached to a tubular shaft by other means and methods. For example, it is expressly contemplated that an adhesive may be utilized for joining the cannula tip to the tubular shaft. It is further contemplated that in some embodiments of the invention the cannula tip may be attached to the tubular shaft by another mechanical joining arrangement such as a crimp joint, a snap connection, a pin connection, or retainer ring. In yet another embodiment, the cannula tip may be attached to the tubular shaft by a process such as welding or brazing.

Figure 15:
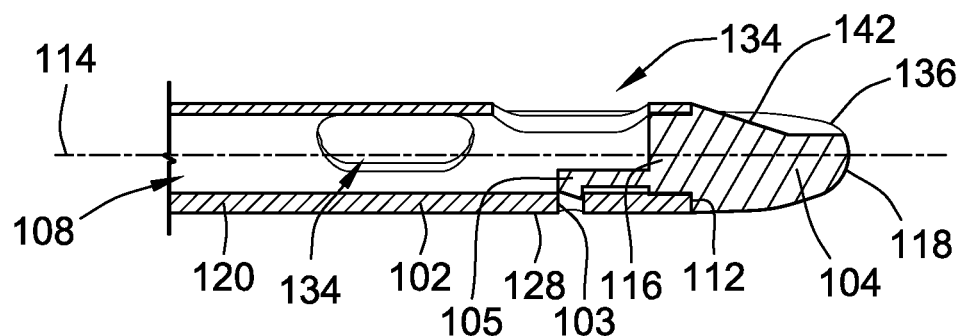
FIGS. 15 and 16 are cross-sectional and enlarged views corresponding to FIG. 3 and illustrating variations of the first exemplary embodiment of the surgical cannula shown in FIG. 1-7 in which the cannula tip is attached to the cannula shaft respectively by a snap-action locking tang arrangement in FIG. 15, and by a locking pin arrangement in FIG. 16.

FIG. 15, for example, shows an variation of the first exemplary embodiment of the surgical cannula 100 in which the cannula tip 104 is attached to the tubular shaft 102 by a snap-action tang locking tang 105 extending from the tip 104 which locks into a tang-retention through-hole 103 in the tubular shaft 102. The locking tang 105 is configured to be deflectable inward as the tip 104 is inserted into the tubular shaft 102. When the distal end of the locking tang 105 has been inserted into the tubular shaft 102 far enough to bring the distal end of the locking tang 105 into alignment with the through-hole 103, the locking tang springs outward. The distal end of the locking tang 105 is configured to form a hook configured for engaging and locking the tip 104 in to the tubular shaft 102 when the hook is aligned with the through-hole 103.

Figure 16:
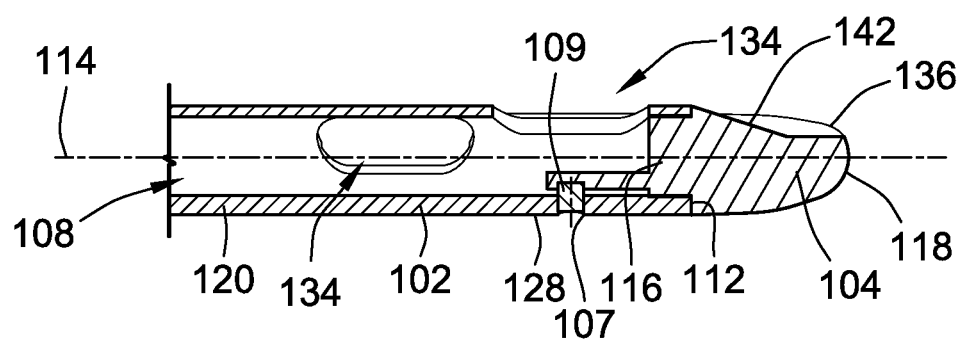
Figure 17:
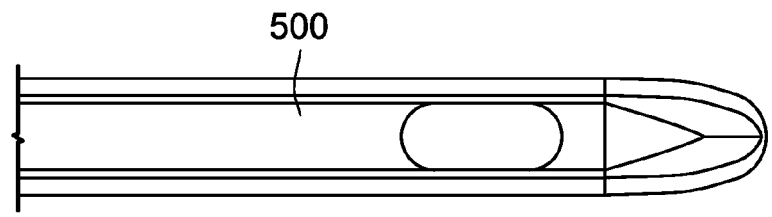
FIGS. 17-22 are partial enlarged views of several alternate exemplary embodiments of the invention, showing a few of the many various combinations of ribbed tips, ribbed tubular shafts and aperture locations and shapes contemplated within the scope of the invention, with FIGS. 20 and 21 showing side and bottom views of the same embodiment, and FIGS. 17-19 and 22 showing side views of different exemplary embodiments.
Figure 18:
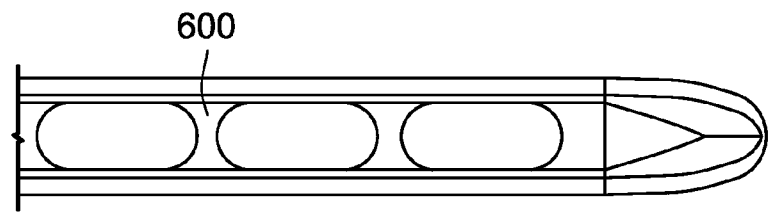
Figure 19:
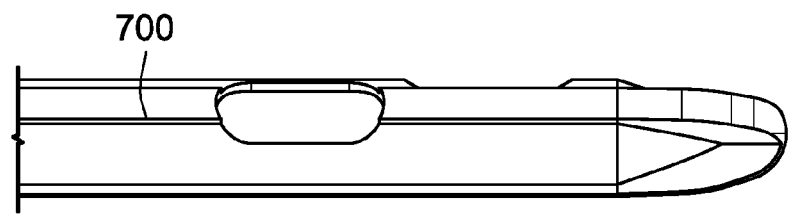
Figure 20:
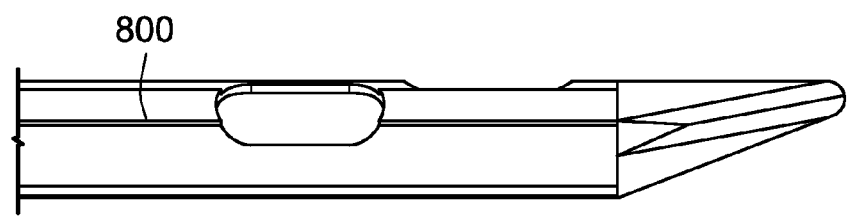
Figure 21:
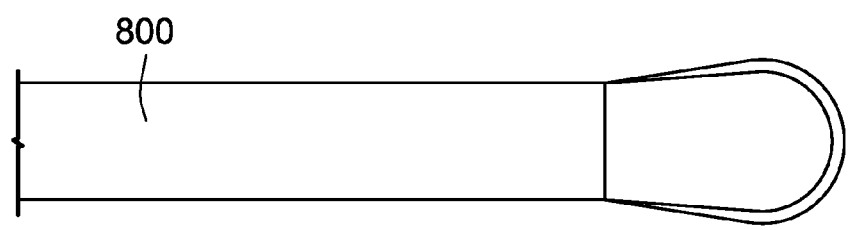
Figure 22:
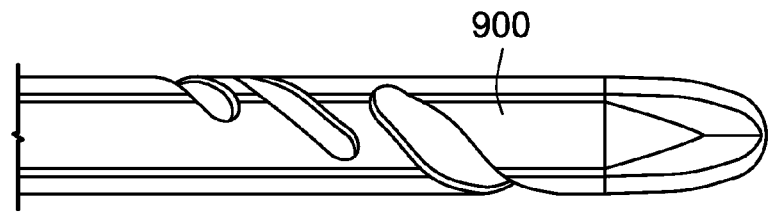

FIG. 16, for example, shows another variation of the first exemplary embodiment of the surgical cannula 100 in which the cannula tip 104 is attached to the tubular shaft 102 by a locking pin 107 which extends through a through-hole in the wall of the tubular shaft 102 and into a locking pin receptacle 109 in the tip 104. The locking pin 107 is sized to create a press fit between the locking pin 107 and either or both of the through-hole in the tubular shaft 102 and the locking pin receptacle 109, to thereby retain the tip 104 in the tubular shaft 102. The pin 107 and or tip 104 may also be retained through the use of an adhesive in addition to, or in lieu of, having a press fit between the pin 107 and the through-hole or the locking pin receptacle 109. As best seen in FIG. 5, the tubular shaft 102 of the first exemplary embodiment of the invention has a wall 120 extending about and along the longitudinal axis 114, with the wall 120 having an inner surface 122 defining the bore 108 in the tubular shaft 102 and an outer surface 124. The outer surface 124 of the tubular shaft 102, in the first exemplary embodiment 100 of the surgical cannula 100, also defines three outwardly projecting ribs 126, 128, 130. These outwardly projecting ribs 126, 128, 130 extend substantially longitudinally along the entire outer surface 124 of the tubular shaft 102 in the first exemplary embodiment of the surgical cannula 100. It will be understood, that although the first exemplary embodiment of the surgical cannula 100 includes three outwardly projecting ribs 126, 128, 130, other embodiments of the invention may include fewer or more than three ribs.

FIG. 6 shows an alternate embodiment of the tubular shaft 102 of the first exemplary embodiment of the surgical cannula 100, in which the bore 108 includes three lobes 132 which extend outward into the three outwardly projecting ribs 126, 128, 130, in such a manner that the bore 108 has an irregular shape, rather than the essentially cylindrical shaped bore 108 of the embodiment shown in FIG. 5. Those skilled in the art will recognize that the alternate embodiment of the tubular shaft 102 shown in FIG. 6 results in the bore 108 having a larger cross-sectional area than the cylindrical shaped bore of the embodiment shown in FIG. 5. It will be appreciated that the larger shaped bore of the embodiment of FIG. 6 provides an increased area within the bore for the passage of fluids and tissue being aspirated from an operative site, or for fluids being infiltrated into the operative site, thereby improving the performance of the cannula 100.

As shown in FIGS. 1-4, the tubular shaft 102 of the first exemplary embodiment of the surgical cannula 100 includes a plurality of apertures 134 extending through the wall 120 of the tubular shaft 102 to thereby provide fluid communication between the bore 108 and the ambient environment surrounding the tubular shaft 102. In the first exemplary embodiment of the surgical cannula 100, these apertures 134 are disposed in relation to rib 128. A portion of the outer surface of the rib 128 is treated with a surface texture, and/or a unique color, as compared to the other ribs 126, 130 in such a manner that the position of the apertures 134 can be determined from the orientation of the visually and/or tactilely discernable rib 128, while the apertures 134 are inserted beneath the skin of a patient and thus not visible to the surgeon.

As best seen in FIGS. 3 and 7, the cannula tip 104, of the first exemplary embodiment of the surgical cannula 100, includes three rib tips 136, 138, 140, with each of the plurality of rib tips 136, 138, 140, corresponding to and extending a respective one of the plurality of ribs 126, 128, 130 of the tubular shaft 102 along the cannula tip 104 from the proximal end 116 to the distal end 118 of the cannula tip 104.

As shown in FIGS. 1, 2, 3, 4 and 7, the rib tips 136, 138, 140, extending along the cannula tip 104, converge with one another at the distal end 118 of the cannula tip 104. As further illustrated in those figures, the converging rib tips 136, 138, 140 of the first exemplary embodiment of the surgical cannula 100 define a blunted surface at the distal end 118 of the cannula tip 104. It will be understood, however, that in other embodiments of the invention the rib tips need not all converge with one another, or form a blunted surface at the distal end of the cannula tip.

As best seen in FIGS. 3 and 4, in the cannula tip 104 of the exemplary embodiment of the surgical cannula 100, the cannula tip 104 defines a substantially conical outer surface portion 142 thereof between the rib tips 136, 138, 140. It will be appreciated, by those having skill in the art, that the blunted distal end of the cannula tip 104 and the conical shaped surface 142 of the tip 104 provide enhanced safety of use, and reduced fatigue for the surgeon manipulating the cannula. Specifically, the blunted tip is less likely to puncture skin, muscle tissue, organs, etc. around the surgical site. The blunted tip is still sharp enough, however, to facilitate pushing the tip of the cannula through fatty tissue at the operative site to facilitate removal of that tissue, or creation of cavities for infiltration of fluid. The conical shaped surface 142 provides reduced friction to aid in pushing the tip of the cannula into the tissue to be removed.

It will be understood, however, that in other embodiments of the invention a cannula tip 104 may have a different shape in the area 142 within the ribs. For example, this area may be concave, convex or any other appropriate shape within the scope of the invention. As shown in FIG. 4 where the area 142 between the rib tips 136, 138, 140 is substantially conical shaped, it is contemplated that a conic angle 144 in the range of 10 degrees to 30 degrees may be preferable to reduce fatigue for the surgeon manipulating the cannula.

The first exemplary embodiment of the surgical cannula 100, FIG. 5, may also include a low-friction coating (not shown) on all, or a portion of at least one of the inner and outer surfaces 122, 124 of the tubular shaft 102. All or a portion of the cannula tip 104 may also include such a low-friction coating (not shown), in the first exemplary embodiment of the surgical cannula 100. Some embodiments of the invention may also include a low friction filler on or inside of a portion of the surgical cannula 100, or at junctures, for example, between the various components of the surgical cannula 100.

As shown in FIGS. 1 and 2, the handle arrangement 106 of the first exemplary embodiment of the surgical cannula 100 is attached to the proximal end 110 of the tubular shaft 102. In the embodiment shown in FIGS. 1 and 2, the wall 120 and outside surface 124 of the tubular shaft are smooth adjacent to the proximal end 110 of the tubular shaft 102. For such embodiments, the assembly of the tubular shaft 102 and the handle 106 may be accomplished by a variety of methods, such as adhesively bonding the shaft 102 within the handle 106. The handle 106 may also be tightly joined to the tubular shaft 102 by a press-fit, a shrink-fit, molding the handle about the tubular shaft or any other appropriate method. It is also contemplated that, in some embodiments of the invention, it may be desirable to roughen the outer surface 124 of the tubular shaft 102 in the region where the handle 106 is to be attached, by knurling for example, to strengthen the juncture of the handle 106 and the outer surface 124 of the tubular shaft, providing enhanced resistance against having the tubular shaft 102 be pulled out of the handle 106 during use of the cannula 100. In yet other embodiment of the invention, it is contemplated that other approaches to enhancing retention of the tubular shaft 102 within the handle 106 may include forming features such as bead on the outside surface 124 of the tubular shaft 102 where it will be encased by the handle 106, or flaring the proximal end 110 of the tubular shaft 106.

The handle arrangement 106 of the first exemplary embodiment of the surgical cannula 100 defines a connector, in the form of a hose barb 146, and a fluid passage 148 extending through the hose barb 146 and the handle 106 in sealed fluid communication with the bore 108 of the tubular shaft 102. The hose barb 146 is configured for attachment of the first exemplary embodiment of the surgical cannula 100 to surgical tubing which is in turn connected to a source of vacuum, a tissue collection arrangement, and/or a source of pressurized infiltration fluid.

A shown in FIG. 1, the handle 106 may include some form of tactilely or visually discernable indicia 150 which is aligned with the tactilely or visually discernable surface treatment and/or rib 128, so that the surgeon may ascertain the orientation of the apertures 134 from looking at and/or feeling the indicia 150 on the handle.

Although the first exemplary embodiment of the surgical cannula 100, described above, includes an integral handle arrangement 106, it will be understood that in other embodiments of the invention a tubular shaft 102 and cannula tip 104 in accordance with the invention may be utilized with efficacy in forms that do not include an integral handle. For example, FIG. 8 shows a second exemplary embodiment of a surgical cannula 200, wherein a Luer fitting 202 is attached to the proximal end of the tubular shaft 102, so that the surgical cannula 200 can be attached to a removable handle or syringe 204 illustrated by dashed lines in FIG. 8.

In similar fashion, FIG. 9 shows a third exemplary embodiment of a surgical cannula 300, according to the invention, in which the proximal end of the tubular shaft 102 is attached to a Toomey hub 302, so that the surgical cannula 300 can be attached to a Toomey syringe as indicated by dashed lines 304 in FIG. 9.

It is contemplated that use of the present invention is not limited to a surgical cannula having an integral handle, Luer fitting, and/or Toomey hub, in accordance with the exemplary embodiments 100, 200, 300 described herein, but may include any appropriate connector or handle structure in accordance with the invention.

It is further contemplated that, in some embodiments of the invention, one or more of the components of the surgical cannula may be formed from a material which cannot withstand steam sterilization, such as: high density polyethylene (HDPE).

Preferably, such a material should be selected such that exposure to steam sterilization will deform the portion of the cannula which is not capable of withstanding steam sterilization to such a degree that the surgical cannula is no longer usable. For example, with reference to the embodiment 100 shown in FIGS. 1-7, it is contemplated that a portion of one or more of the tubular shaft 102, the cannula tip 104, or the handle arrangement 106 may be formed form a material that cannot withstand steam sterilization. In similar fashion, with regard to the embodiments shown in FIGS. 8 and 9, it is contemplated that a portion of one or more of the tubular shaft 102, the cannula tip 104, the Luer fitting 202, and/or the Toomey hub 302 may be formed from the material which cannot withstand steam sterilization.

By forming at least a portion of a surgical cannula, in accordance with the invention, from a material which will not withstand steam sterilization, the surgical cannula becomes non-reusable. Although a non-reusable surgical cannula in accordance with the invention is formed from a material which will not withstand steam sterilization, it is preferred that such a non-reusable cannula would be amenable to sterilization by other sterilization methods known in the art, including but not limited to: EtO; gamma radiation; and hydrogen peroxide sterilization.

In forms of the invention wherein the surgical cannula according to the invention is reusable, the components of the reusable cannula may be formed from a material such as, aluminum or stainless steel, nitinol, titanium, or injection molded from a thermo-plastic capable of withstanding sterilization by EtO, gamma, hydrogen peroxide and steam sterilization.

In either a reusable, or a non-reusable form, it may be desirable to form a surgical cannula, according to the invention, at least partly from a non-metallic material. Where such non-metallic materials are utilized for the cannula tip and the tubular shaft, it is contemplated that these portions of a cannula, according to the invention, may be formed from a material which is radio opaque, to facilitate in location of any portion of the cannula which may become separated from the remainder of the cannula while the tip and tubular shaft of the cannula are inserted within the patient.

Figure 14:
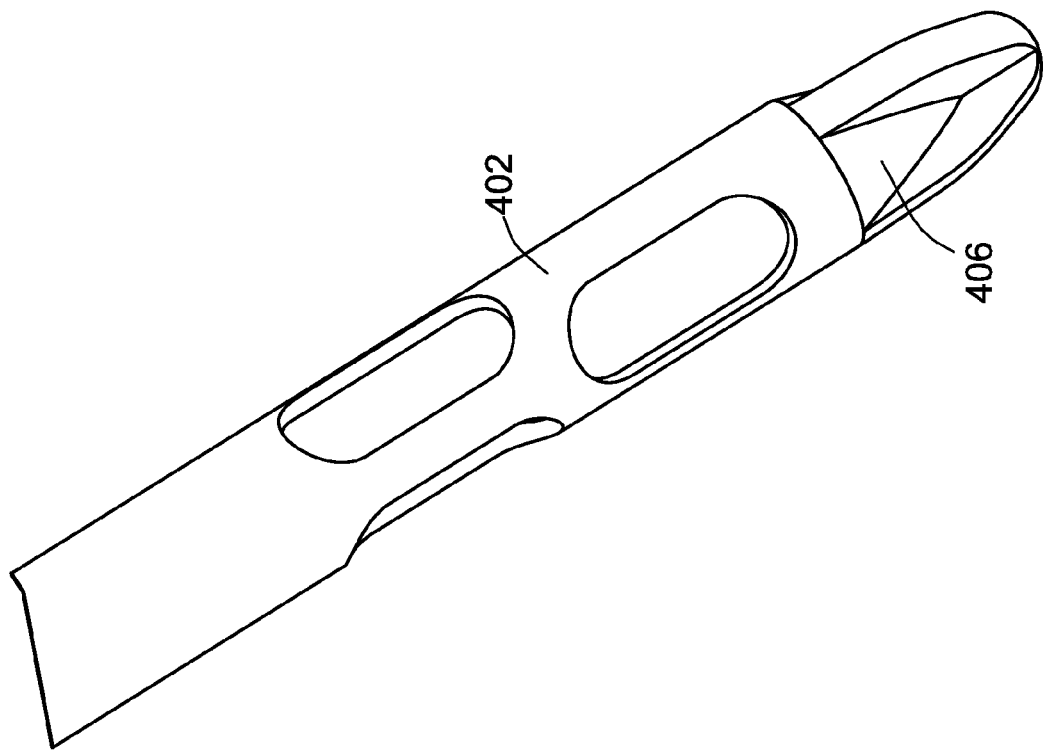
Figure 12:
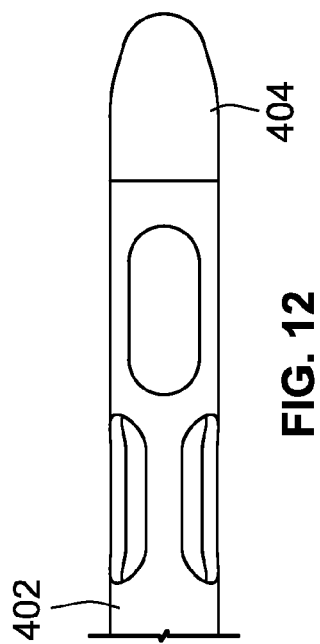
Figure 13:
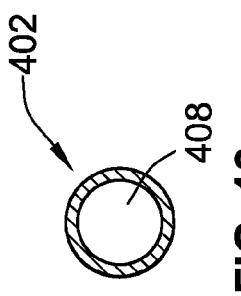

FIGS. 10-14 illustrate a fourth exemplary embodiment of a surgical cannula 400, in accordance with the invention, which is substantially identical to the first embodiment of the surgical cannula 100, described hereinabove with reference to FIGS. 1-7, except that the fourth exemplary embodiment of the cannula 400 does not include any ribs on the outside of the tubular shaft 402 and may or may not include any rib tips on the cannula tip 404 of the surgical cannula 400. The surgical cannula 400 may include any or all of the other aspects of a cannula, according to the invention, within the scope of the invention. FIG. 12 shows an enlarged partial view of a version of the fourth exemplary embodiment of the surgical cannula 400 in which both the tubular shaft 402 and the tip 404 do not include any ribs. FIG. 14 shows an enlarged, partial perspective view of another version of the fourth exemplary embodiment of the surgical cannula 400 in which a ribbed tip 406 is used in conjunction with a tubular shaft 402 that does not include ribs.

It is also contemplated that the invention may be practiced in forms having tubular shafts and cannula tips configured in accordance with any appropriate form of cannula tip, including but not limited to those marketed by the Byron Medical Inc., of Tucson, Ariz., and known in the art of cannula tip styles as: Mercedes; Accelerator III™; Las Vegas™; Standard; Gilliland Etching Cannula; Becker™; Becker Teardrop™; Spatula; Keel Cobra; Keel Cobra II; Fournier; Sattler™; or Candy Cane™. For example, FIGS. 17-22 illustrate a few of the wide variety of alternate embodiments of surgical cannulas 500, 600, 700, 800, 900 contemplated within the scope of the invention, in addition to those previously addressed hereinabove.

In accordance with another aspect of the invention, the periphery of one or more apertures in a cannula may be configured to form a cutting edge, to thereby enhance removal of tissue and further reduce the amount of force which must be exerted by a surgeon in cutting or avulsing the tissue to be removed.

As illustrated in FIGS. 23-25, in a typical cannula of the type previously used, or as illustrated for any of the exemplary embodiments of the cannula shown herein in FIGS. 1-22, the tubular shaft 1002 of the cannula 1000 includes a wall 1004 having an inner surface 1006 thereof defining a bore 1008. The wall 1004 of the tubular shaft 1002 also defines an outer surface 1010 of the wall 1004.

In the exemplary embodiment of the cannula 1000 shown in FIGS. 23-25, the cannula 1000 includes an aperture 1012 to allow passage of tissue from the outer surface 1010 of the wall into the bore 1008.

The aperture 1012 defines an aperture periphery 1014 and an aperture edge 1016 extending along the aperture periphery 1014.

In the embodiments shown in FIGS. 23-25, the entirety of the aperture periphery 1014 is configured in such a manner that the aperture edge 1016 is disposed at right angles 1018, 1020, 1022, 1024, to a median plane 1026 extending longitudinally through the tubular shaft 1002 of the cannula 1000. Even where the wall 1004 of the tubular shaft 1002 is relatively thin, the substantially square aperture edge 1016 of the embodiment of the cannular 1000 shown in FIGS. 23-25 is substantially blunt and results in removed tissue being largely torn away from surrounding tissue, rather than being cut away from the surrounding tissue. In some embodiments of a cannula, according to the invention, such a tearing action is advantageous. Accordingly, in practicing the invention, some or all of the apertures in a cannula according to the invention may have the aperture edges configured substantially square with the median plane, in the manner shown in FIGS. 23-25.

As previously stated, however, in some embodiments of a cannula according to the invention it may be desirable to have one or more apertures with edges configured to form a cutting edge. In various embodiments, according to the invention, all of the aperture edge, or only one or more portions of the aperture edge, may be configured to form a cutting edge.

Figure 26:
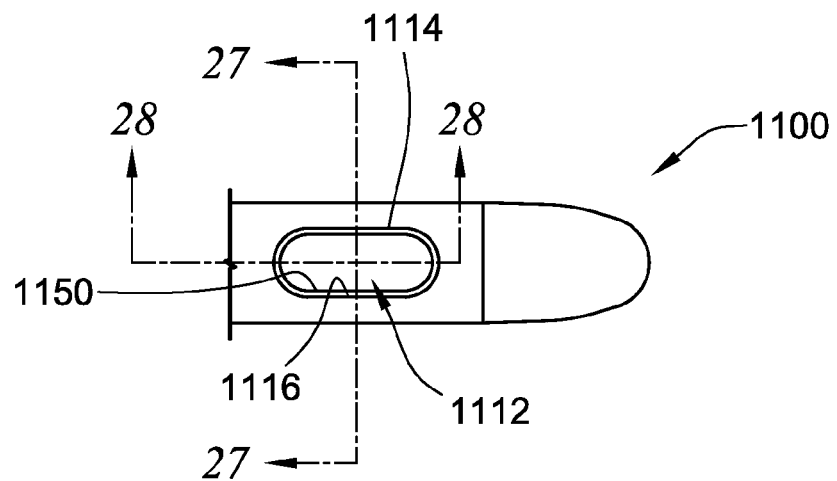
FIGS. 26-28 are enlarged views showing details of an exemplary embodiment of a cannula, according to the invention, in which the entirety of an edge of an aperture of the cannula is oriented at an acute angle to a median plane of the cannula, in order to form a cutting edge extending around the entirety of the periphery of the aperture.
Figure 27:
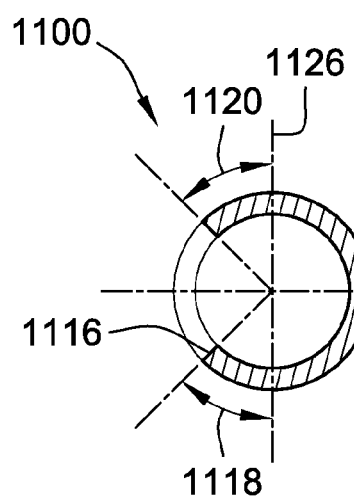
Figure 28:
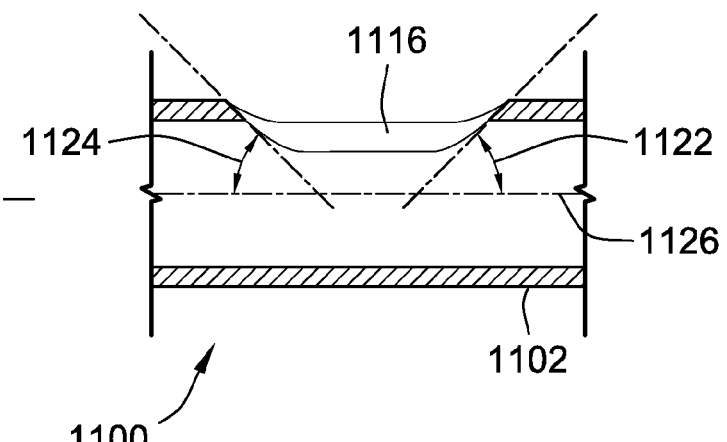

For example, the exemplary embodiment of the cannula 1100 shown in FIGS. 26-28 has an aperture edge 1116 cut at an acute angle 1118, 1120, 1122, 1124 to a median plane 1126, to thereby form a cutting edge 1150 extending around the entirety of the periphery 1114 of an aperture 1112 in the tubular shaft 1102 of the cannula 1100.

Figure 29:
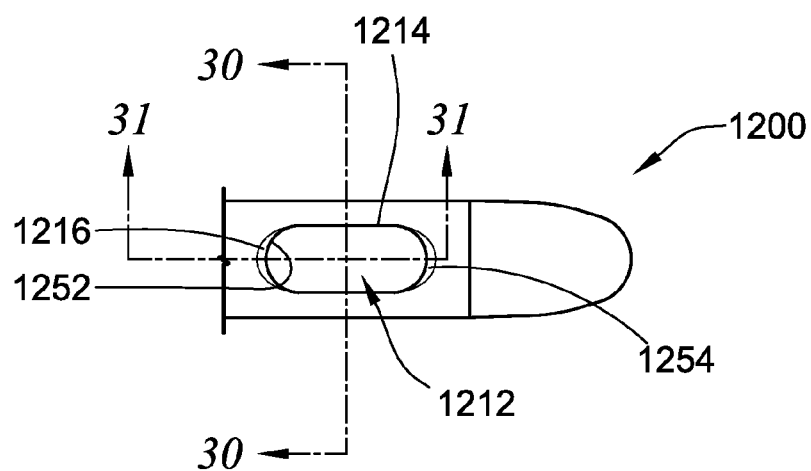
FIGS. 29-31 are partial enlarged views of a portion of a cannula, according to the invention, having opposite axial ends of an elongated aperture formed to provide cutting edges at the two longitudinal ends of the aperture.
Figure 30:
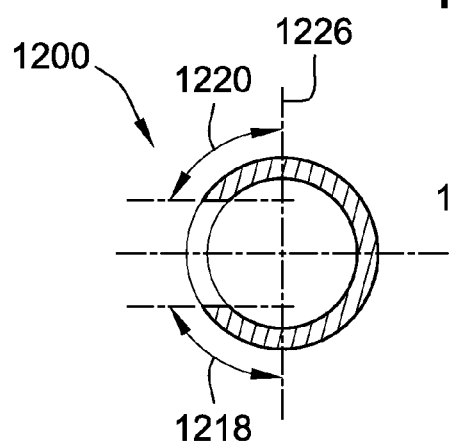
Figure 31:
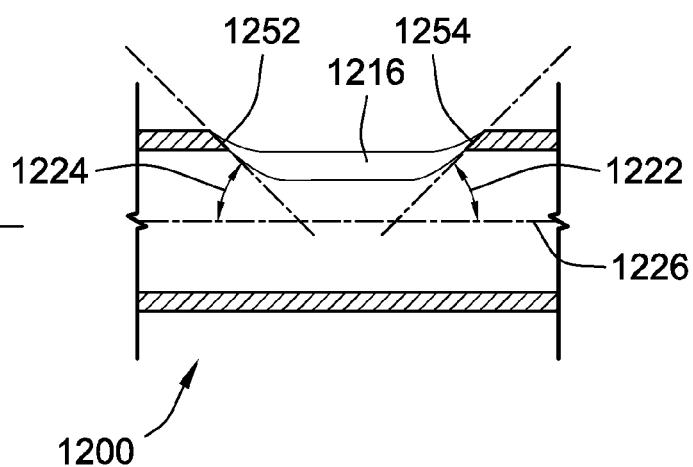

In the exemplary embodiment of the cannula 1200 shown in FIGS. 29-31, only the longitudinal ends of the aperture edge 1216 are configured at an acute angle 1222, 1224, to the median plane 1226, with the side walls of the aperture edge 1214 of the aperture 1212 being configured at right angles 1218, 1220 to the median plane 1226, so that first and second cutting edges 1252, 1254 are formed only at the opposite longitudinal ends of the aperture 1212. With this configuration, the first and second cutting edges 1252, 1254 serve to cut the tissue to be removed as the cannula is moved in a longitudinal direction through the tissue, whereas rotation of the cannula 1200 within the tissue will generally result in the sides of the aperture edge 1214 configured at a right angle 1218, 1220 to the median plane 1226 tearing away or otherwise avulsing the tissue to be removed. It will be understood that, although both longitudinal ends of the aperture edge 1214 of the exemplary embodiment of the cannula 1200 have been configured at the same acute angle to the median plane 1226, in other embodiments of the invention only one the longitudinal ends may be configured to form a cutting edge. It will be further understood that in embodiments of the invention having two or more portions of an aperture edge configured at an angle to form a cutting edge, the angle may not necessarily be the same for each angled portion of the cutting edge. Such a configuration may be selected to provide differing cutting action depending upon the direction of motion of the cannula. The configuration of the cutting edge along various portions of an aperture edge, in a cannula according to the invention, may also be configured in a manner taking into account ergonomic factors making it easier for the surgeon to apply force in one direction of the cannula rather than another, in such a manner that substantially uniform force is required to manipulate the cannula in any of several desired directions.

Figure 32:
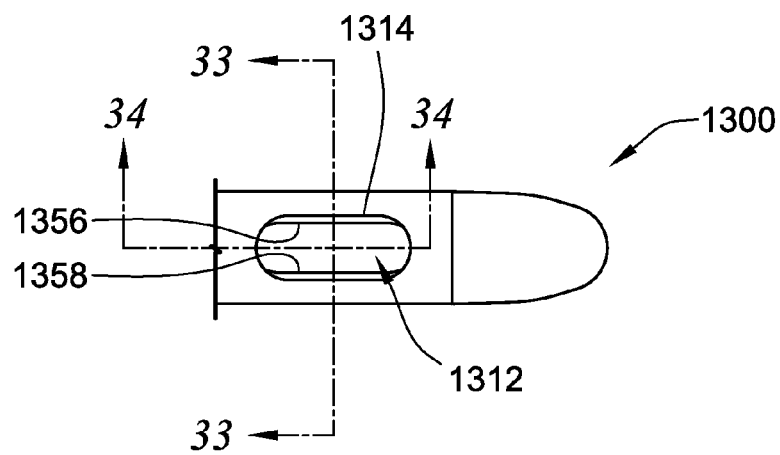
FIGS. 32-34 are enlarged partial views of an exemplary embodiment of a cannula, according to the invention, having longitudinally extending sides of an aperture configured at an acute angle to a median plane of the cannula to thereby form cutting edges extending along the longitudinally extending sides of the aperture.
Figure 33:
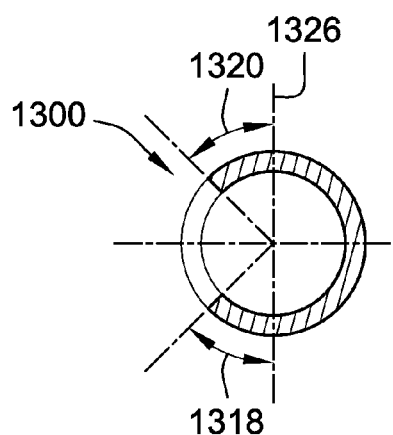
Figure 34:
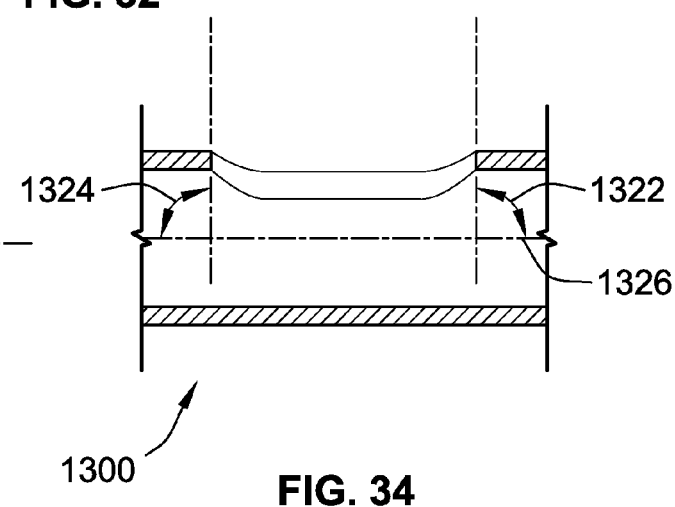

In the embodiment of the cannula 1300 shown in FIGS. 32-34, the longitudinal ends of the aperture edge 1314 are configured at a right angle 1322, 1324 to the median plane 1326, but the portions of the aperture edge 1314 extending along opposite sides of the aperture 1312 between the longitudinal ends of the aperture are configured at an acute angle 1318, 1320 to the median plane 1326, to thereby form a pair of first and second cutting edges 1356, 1358. With this configuration, motion of the cannula 1300 in and out of the tissue along a longitudinal axis of the cannula 1300 results in the longitudinal ends of the aperture 1312 substantially tearing away or otherwise avulsing tissue, whereas side ways movement and/or rotation of the cannula 1300 results in the first and second cutting edges 1356, 1358 providing a cutting action. In the same manner described above with regard to the embodiment of FIGS. 29-31, it will be understood that in practicing the invention the first and second cutting edges 1356, 1358 may be disposed at different acute angles 1318, 1320 from the median plane 1326, or that only one of the sides of the aperture edge 1314 may be configured as a cutting edge.

Figure 35:
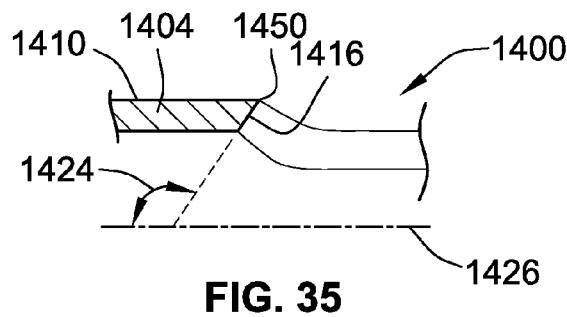
FIG. 35 is an enlarged partial cross-sectional illustration of an embodiment of a cannula, according to the invention, having a cutting edge formed along a portion of the edge of an aperture, by configuring the aperture edge at an obtuse angle to a median plane of the cannula.

It will be understood that, in practicing the invention, a cutting edge may be formed to have any appropriate configuration. Specifically, in practicing the invention, it is not necessary that a cutting edge along the edge of an aperture in a cannula according to the invention be formed by configuring the cutting edge at an acute angle to a median plane as described above with regard to the exemplary embodiments shown in FIGS. 26-34. For example, as shown in FIG. 35, a cutting edge 1450 may be formed along an outer surface 1410 of the wall 1404 of a cannula 1400 by configuring a portion of the aperture edge 1416 at an obtuse angle 1424 (greater than 90°) to the median plane 1426.

Figure 36:
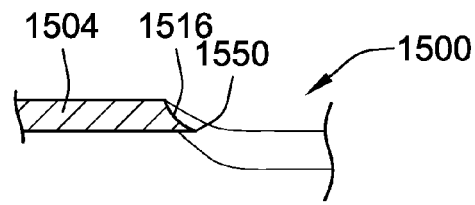
FIG. 36 is an enlarged partial cross-sectional view of an embodiment of a cannula, according to the invention, having a cutting edge along a portion of an aperture formed by configuring the portion of the aperture edge in a curved shape.

As illustrated in FIG. 36, it is also not necessary that a cutting edge be formed by configuring a portion of an aperture edge 1516 at an angle to a central median plane of a cannula 1500, according to the invention. Specifically, as shown in FIG. 36, a portion of the aperture edge 1516 may be configured in any appropriate shape, such as the curved edge illustrated in FIG. 36 to form a cutting edge 1550. It is also contemplated that, in practicing the invention, some embodiments may include an aperture edge having multiple angles or curved sections to provide a desired cutting action.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A surgical cannula comprising:
   an elongated tubular shaft having a wall extending about a longitudinal axis of the cannula, with the wall having an inner surface thereof defining a bore extending longitudinally through the cannula from a proximal to a distal end of the tubular shaft;
   the tubular shaft also having at least one outwardly projecting rib extending substantially longitudinally along an outer surface of the tubular shaft; wherein, the bore includes at least one lobe thereof, with the at least one lobe extending outward into the at least one outwardly projecting rib.

2. The surgical cannula of claim 1, wherein, the bore has a substantially circular cross-sectional shape.

3. The surgical cannula of claim 1, further comprising, one or more apertures through the wall of the tubular shaft.

4. The surgical cannula of claim 3, wherein, each of the one or more apertures defines a respective aperture periphery and an aperture edge extending along the aperture periphery, and at least a portion of the aperture edge of at least one of the one or more apertures is configured to form a cutting edge; wherein: the tubular shaft has a wall extending about the longitudinal axis of the cannula; the wall has an inner surface thereof defining a bore extending longitudinally through the cannula from a proximal to a distal end of the tubular shaft; the wall also has an outer surface thereof extending longitudinally along the cannula from the proximal to the distal end of the tubular shaft; and the tubular shaft also comprises at least one aperture therein extending through the wall of the tubular shaft and defining an aperture edge joining the inner and outer walls along a perimeter of the aperture; with at least a portion of the aperture edge being configured to form a cutting edge along a portion of the periphery of the aperture edge; wherein, the bore includes at least one lobe thereof, with the at least one lobe extending outward into the at least one outwardly projecting rib.

5. The surgical cannula of claim 3, wherein, the apertures are disposed in relation to one of the at least one projecting ribs.

6. The surgical cannula of claim 3, wherein, each of the one or more apertures each defines a respective aperture periphery and an aperture edge extending along the aperture periphery, and at least a portion of the aperture edge of at least one of the one or more apertures is configured to form a cutting edge.

7. The surgical cannula of claim 5, further comprising, a plurality of outwardly projecting substantially longitudinally extending ribs, with the rib from which the apertures are positioned being visually discernible from the other ribs.

8. The surgical cannula of claim 5, further comprising, a plurality of outwardly projecting substantially longitudinally extending ribs, with the rib from which the apertures are positioned being tactilely discernible from the other ribs.

9. The surgical cannula of claim 1, wherein, the bore at the distal end of the tubular shaft is closed by a cannula tip.

10. The surgical cannula of claim 9, wherein, the cannula tip includes apertures extending through a wall of the tubular shaft in fluid communication with the bore in the tubular shaft.

11. The surgical cannula of claim 9, wherein, the cannula tip includes a rib tip extending from a proximal end of the cannula tip attached to the distal end of the tubular shaft.

12. The surgical cannula of claim 11, wherein, the rib tip extends from a proximal end of the cannula tip attached to the distal end of the tubular shaft to a distal end of the cannula tip.

13. The surgical cannula of claim 12, wherein, the tubular shaft includes a plurality of longitudinally extending ribs, and the cannula tip includes a plurality of rib tips, with each of the plurality of rib tips of the cannula tip corresponding to and extending one of the plurality of ribs of the tubular shaft along the cannula tip from the proximal to the distal end of the cannula tip.

14. The surgical cannula of claim 13, wherein, the rib tips extending along the cannula tip converge with one another at the distal end of the cannula tip.

15. The surgical cannula of claim 14, wherein, the rib tips define a blunted surface at the distal end of the cannula tip.

16. The surgical cannula of claim 15, wherein, the cannula tip defines a substantially conical outer surface thereof between the rib tips.

17. The surgical cannula of claim 16, wherein, the conical surface defines a conic angle in the range of 10 degrees to 30 degrees.

18. The surgical cannula of claim 15, wherein, the cannula tip defines a substantially conical outer surface thereof between the rib tips.

19. The surgical cannula of claim 15, wherein, the cannula tip defines a substantially convex curved outer surface thereof between the rib tips.

20. The surgical cannula of claim 1, further comprising, a tip closing the bore at the distal end of the tubular shaft, with the tip being joined to the tubular shaft by a mechanical connection.

21. The surgical cannula of claim 1, further comprising, a tip closing the bore at a distal end of the tubular shaft, with the tip being joined to the tubular shaft by an adhesive.

22. The surgical cannula of claim 1, wherein, at least one of the inner and outer surfaces of the tubular shaft includes a low-friction coating.

23. The surgical cannula of claim 22, further comprising, a cannula tip closing the bore in the tubular shaft at a distal end of the tubular shaft, with the cannula tip and cannula shaft having at least a portion thereof including a low-friction coating.

24. The surgical cannula of claim 1, further comprising, a cannula tip closing the bore at the distal end of the tubular shaft, wherein the cannula tip is formed from a non-metallic material.

25. The surgical cannula of claim 24, wherein, the cannula tip is radio opaque.

26. The surgical cannula of claim 1, further comprising, at least one portion thereof which is not steam sterilizable.

27. A surgical cannula comprising, a tubular shaft defining a bore therein extending from a proximal to a distal end of the tubular shaft along a longitudinal axis of the cannula, and a cannula tip closing the bore at the distal end of the tubular shaft, with at least a portion of the tubular shaft and cannula tip being formed from a material which cannot withstand steam sterilization, the cannula tip being attached to the tubular shaft by one of a mechanical connection and an adhesive connection.

28. The surgical cannula of claim 27, wherein, exposure to steam sterilization will deform the portion of the cannula shaft and cannula tip not capable of withstanding steam sterilization to the degree that the surgical cannula is no longer usable.

29. The surgical cannula of claim 28, further comprising, a handle arrangement attached to the proximal end of the tubular shaft, wherein the handle, tubular shaft and cannula tip are at least partly formulated from a material which is not steam sterilizable.

30. The surgical cannula of claim 27, further comprising a connector attached to the proximal end of the tubular shaft and having a fluid passage defined thereby connected in fluid communication with the bore in the tubular shaft.

31. The surgical cannula of claim 30, wherein, the connector comprises a connector from the group consisting of:
a hose barb;
a Toomey hub;
and a Luer lock.

32. The surgical cannula of claim 31, wherein, the connector is part of a handle attached to the proximal end of the tubular shaft.

33. A surgical cannula comprising:
an elongated tubular shaft having a wall extending about a longitudinal axis of the cannula, with the wall having an inner surface thereof defining a bore extending longitudinally through the cannula from a proximal to a distal end of the tubular shaft; and
a tip closing the bore at the distal end of the tubular shaft, with the tip being joined to the tubular shaft by a mechanical connection; wherein, the tubular shaft further comprises at least one outwardly projecting rib extending substantially longitudinally along an outer surface of the tubular shaft.

34. The surgical cannula of claim 33, wherein:
the wall also has an outer surface thereof extending longitudinally along the cannula from the proximal to the distal end of the tubular shaft; and
the tubular shaft also comprises at least one aperture therein extending through the wall of the tubular shaft and defining an aperture edge joining the inner and outer surfaces of the wall along a perimeter of the aperture;
with at least a portion of the aperture edge being configured to form a cutting edge along a portion of the periphery of the aperture edge.

35. The surgical cannula of claim 33, wherein, the mechanical connection comprises, a snap-fit locking arrangement for fixedly connecting the tip to the distal end of the tubular shaft.

36. The surgical cannula of claim 35, wherein, the tip further comprises one or more rib tips extending from an outer surface thereof.

37. The surgical cannula of claim 35, wherein, the tubular shaft further comprises at least one outwardly projecting rib extending substantially longitudinally along an outer surface of the tubular shaft.

38. The surgical cannula of claim 33, wherein, the mechanical connection comprises, a locking-pin arrangement for fixedly connecting the tip to the distal end of the tubular shaft.

39. A surgical cannula comprising:
an elongated tubular shaft having a wall extending about a longitudinal axis of the cannula;
the wall having an inner surface thereof defining a bore extending longitudinally through the cannula from a proximal to a distal end of the tubular shaft, the bore including at least one outward-extending lobe thereof;
the wall also having an outer surface thereof extending longitudinally along the cannula from the proximal to the distal end of the tubular shaft;
the tubular shaft also having at least one aperture therein extending through the wall of the tubular shaft and defining an aperture edge joining the inner and outer walls along a perimeter of the aperture;
with at least a portion of the aperture edge being configured to form a cutting edge along a portion of the periphery of the aperture edge; wherein, the periphery of the aperture edge defines first and second longitudinal ends of the aperture edge, and the cutting edge extends at least partly along at least one of the first and second longitudinal ends of the aperture edge; wherein, the periphery of the aperture edge defines first and second longitudinally extending sides of the aperture edge, and the cutting edge extends at least partly along at least one of the first and second longitudinally extending sides of the aperture edge.

40. The surgical cannula of claim 39, wherein, the entire aperture edge is configured to form the cutting edge.

* * * * *

UNITED STATES PATENT AND TRADEMARK OFFICE
CERTIFICATE OF CORRECTION

PATENT NO. : 8,591,480 B2  
APPLICATION NO. : 12/814971  
DATED : November 26, 2013  
INVENTOR(S) : Gregory S. Marler Page 1 of 1

It is certified that error appears in the above-identified patent and that said Letters Patent is hereby corrected as shown below:

In the Claims:

Column 14, lines 20-34, Claim 4, delete
"wherein: the tubular shaft has a wall extending about the longitudinal axis of the cannula;the wall has an inner surface thereof defining a bore extending longitudinally through the cannula from a proximal to a distal end of the tubular shaft;the wall also has an outer surface thereof extending longitudinally along the cannula from the proximal to the distal end of the tubular shaft; and the tubular shaft also comprises at least one aperture therein extending through the wall of the tubular shaft and defining an aperture edge joining the inner and outer walls along a perimeter of the aperture;with at least a portion of the aperture edge being configured to form a cutting edge along a portion of the periphery of the aperture edge;wherein, the bore includes at least one lobe thereof, with the at least one lobe extending outward into the at least one outwardly projecting rib."

Column 15, line 53, Claim 27, delete ".", should be changed to --;--.

Column 15, line 53, add to Claim 27
"wherein:
the tubular shaft has a wall extending about the longitudinal axis of the cannula;
    the wall has an inner surface thereof defining a bore extending longitudinally through the cannula from a proximal to a distal end of the tubular shaft;
    the wall also has an outer surface thereof extending longitudinally along the cannula from the proximal to the distal end of the tubular shaft; and
    the tubular shaft also comprises at least one aperture therein extending through the wall of the tubular shaft and defining an aperture edge joining the inner and outer walls along a perimeter of the aperture;
    with at least a portion of the aperture edge being configured to form a cutting edge along a portion of the periphery of the aperture edge;
    wherein, the bore includes at least one lobe thereof, with the at least one lobe extending outward into the at least one outwardly projecting rib."

Signed and Sealed this  
Sixth Day of May, 2014

Michelle K. Lee  
*Deputy Director of the United States Patent and Trademark Office*